(12) United States Patent
Knoll

(10) Patent No.: US 10,349,849 B2
(45) Date of Patent: Jul. 16, 2019

(54) METHOD, LOGIC UNIT AND SYSTEM FOR DETERMINING A PARAMETER REPRESENTATIVE FOR THE PATIENT'S VOLUME RESPONSIVENESS

(71) Applicant: PHILIPS MEDIZIN SYSTEME BÖBLINGEN GMBH, Böblingen (DE)

(72) Inventor: Reinhold Knoll, Neuburg (DE)

(73) Assignee: PHILIPS MEDIZIN SYSTEME BÖBLINGEN, Böblingen (DE)

( * ) Notice: Subject to any disclaimer, the term of this patent is extended or adjusted under 35 U.S.C. 154(b) by 111 days.

(21) Appl. No.: 14/761,654

(22) PCT Filed: Jan. 9, 2014

(86) PCT No.: PCT/EP2014/000032
§ 371 (c)(1),
(2) Date: Jul. 17, 2015

(87) PCT Pub. No.: WO2014/114424
PCT Pub. Date: Jul. 31, 2014

(65) Prior Publication Data
US 2015/0359442 A1 Dec. 17, 2015

Related U.S. Application Data

(60) Provisional application No. 61/756,891, filed on Jan. 25, 2013.

(30) Foreign Application Priority Data

Jan. 25, 2013 (EP) .................................... 13000375

(51) Int. Cl.
*A61B 5/02* (2006.01)
*A61B 5/0295* (2006.01)
(Continued)

(52) U.S. Cl.
CPC .......... *A61B 5/0295* (2013.01); *A61B 5/0205* (2013.01); *A61B 5/029* (2013.01);
(Continued)

(58) Field of Classification Search
CPC .............. A61B 5/0205; A61B 5/02108; A61B 5/02225; A61B 5/029; A61B 5/0295
See application file for complete search history.

(56) References Cited

U.S. PATENT DOCUMENTS

| 5,769,082 A | 6/1998 | Perel |
| 7,422,562 B2 | 9/2008 | Hatib et al. |

(Continued)

FOREIGN PATENT DOCUMENTS

EP 0078090 A1 5/1983

OTHER PUBLICATIONS

Cannesson et al., Pulse pressure variation: where are we today? J. Clin. Monitor. Comput., 25:45-56 (2011).
(Continued)

*Primary Examiner* — Puya Agahi

(57) ABSTRACT

The invention refers to a method of determining an indicator that is representative for a patient's volume responsiveness, comprising the following steps: (i) measuring a sequence of pulse signals of a patient; (ii) determining an envelope (signal)-curve based on the sequence of measured pulse signals; (iii) determining a fit(envelope(signal))-function based on the previously determined envelope(signal)-curve, the fit(envelope(signal))-function representing an idealized curve progression of the envelope(signal)-curve without comprising pulse variations caused by ventilation or respiration induced heart-lung interaction; (iv) determining respiratory pulse variation signals corresponding to the pulse variations caused by ventilation or respiration induced heart-lung interaction; (v) determining an envelope(respiration)-
(Continued)

curve based on the previously determined respiratory pulse variation signals; (vi) determining a fit(envelope(respiration))-function based on the previously determined envelope (respiration)-curve, the fit(envelope(respiration))-function representing an idealized curve progression of the envelope (respiration)-curve; (vii) determining the indicator that is representative for the patient's volume responsiveness based on the fit(envelope(signal))-function and the fit(envelope(respiration))-function. The invention also relates to a logic unit and a system, both for determining an indicator representative for the patient's volume responsiveness.

20 Claims, 3 Drawing Sheets

(51) Int. Cl.
    *A61B 5/00*        (2006.01)
    *A61B 5/0205*    (2006.01)
    *A61B 5/021*     (2006.01)
    *A61B 5/029*     (2006.01)
    *A61B 5/08*      (2006.01)
    *A61B 5/022*     (2006.01)
    *A61B 5/024*     (2006.01)

(52) U.S. Cl.
    CPC ........ *A61B 5/02108* (2013.01); *A61B 5/0816* (2013.01); *A61B 5/725* (2013.01); *A61B 5/7246* (2013.01); *A61B 5/7278* (2013.01); *A61B 5/02225* (2013.01); *A61B 5/02405* (2013.01); *A61B 5/08* (2013.01); *A61B 5/6824* (2013.01)

(56) References Cited

U.S. PATENT DOCUMENTS

| | | | |
|---|---|---|---|
| 2001/0049476 A1* | 12/2001 | Forstner | A61B 5/02225 600/494 |
| 2004/0024323 A1* | 2/2004 | Kulik | A61B 5/02225 600/490 |
| 2008/0033306 A1 | 2/2008 | Joeken | |
| 2011/0270097 A1* | 11/2011 | Aboy | A61B 5/02116 600/484 |
| 2012/0023041 A1* | 1/2012 | Kariv | G06F 11/3447 706/12 |

OTHER PUBLICATIONS

Gouvêa et al., Evaluation of the pulse pressure variation index as a predictor of fluid responsiveness during orthotopic liver transplantation, Br. J. Anaesthesia, 103: 238-43 (2009).

International Search Report and Written Opinion, International Application No. PCT/EP2014/000032, dated Feb. 28, 2014.

Michard et al., Using heart-lung interactions to assess fluid responsiveness during mechanical ventilation, Crit. Care, 4:282-9 (2000).

* cited by examiner

METHOD, LOGIC UNIT AND SYSTEM FOR DETERMINING A PARAMETER REPRESENTATIVE FOR THE PATIENT'S VOLUME RESPONSIVENESS

CROSS-REFERENCE TO RELATED APPLICATIONS

This is the U.S. national phase of PCT/EP2014/000032, filed Jan. 9, 2014, which claims the benefit of European Patent Application No. 13000375.9, filed Jan. 25, 2013 and U.S. Patent Application No. 61/756,891, filed Jan. 25, 2013.

FIELD OF THE INVENTION

The present disclosure relates to a method of determining an indicator that is representative for volume responsiveness of a patient. The disclosure also relates to a logic unit and a corresponding system for determining the indicator representative for the patient's volume responsiveness.

BACKGROUND

In the past, the concept of volume responsiveness (sometimes also called "fluid responsiveness") has been increasingly used in order to optimize the fluid management of patients, in particular of critically ill and/or anesthetised patients. According to this concept, a patient whose stroke volume, i.e. the amount of blood expelled by a ventricle of the heart during systole, increases significantly after fluid administration has "high" volume responsiveness. In contrast, a patient whose stroke volume hardly increases after fluid administration exhibits "low" or no volume responsiveness. Whether an increase in cardiac output will occur upon fluid administration depends mostly on the position of an individual patient on the so-called "Frank-Starling curve". As schematically illustrated in FIG. 2, the Frank-Starling curve plots the preload against stroke volume, wherein by "preload" the volumetric pressure is meant that stretches the right or left ventricle of the heart to its largest geometric dimensions at the end of the diastole. Notably, the Frank-Starling curve is not linear but exhibits a characteristic concave shape, with the initial part being relatively steep and becoming progressively flat thereby reaching a plateau.

Achieving an increase in cardiac output usually results in an optimization of tissue perfusion which is a major goal of fluid therapy. As described for example by G. Gouvêa et al. in the British Journal of Anaesthesia (2009), 103: 238-43, "Evaluation of the pulse pressure variation index as a predictor of fluid responsiveness during orthotopic liver transplantation" and also by M. Cannesson et al. in the Journal of Clinical Monitoring and Computing (2011), 25: 45-56, "Pulse pressure variation: where are we today?", if the patient is on the steep part of the Frank-Starling curve, cardiac output can be efficiently increased by administering fluid. However, if the patient is on the flat part of the Frank-Starling curve, no significant increase in cardiac output will be achieved by administering fluid. Fluid loading in this setting may even be hazardous for the patient and cause peripheral or pulmonary edema. Therefore, it is of major importance to reliably determine the position of the patient on the Frank-Starling curve, i.e. to determine the patient's volume responsiveness, before introducing fluid into the patient's circulation.

Since there is no straight-forward method available to measure the preload and the stroke volume of a patient's heart directly, i.e. to measure the patient's volume responsiveness, intensive studies have been carried out during the last decades to identify another indicator based on measurable parameters to predict the volume responsiveness of a patient.

As described for example by F. Michard et al. in Crit Care (2000), 4: 282-289, "Using heart-lung interactions to assess fluid responsiveness during mechanical ventilation", in mechanically ventilated patients, the magnitude of the respiratory changes in left ventricle stroke volume can be used to assess volume responsiveness. Intermittent positive-pressure ventilation induces cyclic changes in the loading conditions of right and left ventricles. Mechanical insufflation decreases preload and increases afterload of the right ventricle. Right ventricular preload reduction is due to a decrease in the venous return pressure gradient that is related to the inspiratory increase in pleural pressure during mechanical positive pressure ventilation. The concomitant increase in right ventricular afterload is related to the inspiratory increase in trans-pulmonary pressure caused by the ventilation induced increase in airway pressure. Reduction in right ventricular preload and increase in right ventricular afterload both lead to a decrease in right ventricular stroke volume, which arises at its minimum at the end of the inspiratory period. The inspiratory impairment in venous return is assumed to be the major mechanism behind the inspiratory reduction in right ventricular stroke volume. The inspiratory reduction in right ventricular stroke volume subsequently leads to a further downstream decrease in left ventricular filling after a phase lag of two to three heart beats because of the blood's trans-pulmonary transit time. Thus, left ventricular preload reduction may induce a decrease in left ventricular stroke volume, which reaches its minimum during the mechanical expiratory period.

Interestingly, the cyclic changes in right ventricle preload induced by mechanical ventilation should result in greater cyclic changes in right ventricular stroke volume when the right ventricle operates on the steep rather than on the flat portion of the Frank-Starling curve. The cyclic changes in right ventricular stroke volume, and hence in left ventricular preload, should also result in larger cyclic changes in left ventricular stroke volume when the left ventricle operates on the ascending, steep portion of the Frank-Starling curve. Thus, the magnitude of the respiratory changes in left ventricular stroke volume which is a major determinant of systolic arterial pressure should be an indicator of volume responsiveness. Therefore, it has been proposed to analyse the respiratory changes in systolic pressure by calculating the difference between maximum and the minimum value of systolic pressure over one single respiratory cycle of a mechanically ventilated patient. This difference has been called "systolic pressure variation" (SPV).

Furthermore, it has been recently proposed that cardiac volume responsiveness may be assessed in a more sophisticated way by calculating the arterial "pulse pressure variation" (PPV). "Pulse pressure" (PP) has been defined as the difference between systolic and diastolic pressure within one single respiratory cycle. Notably, the pulse pressure is almost directly proportional to the stroke volume of the left ventricle. Conventionally pulse pressure variation is calculated using the following formula:

$$PPV = \frac{PP_{max} - PP_{min}}{\frac{1}{2}(PP_{max} + PP_{min})} * 100\%$$

wherein $PP_{max}$ and $PP_{min}$ are the maximal and minimal pulse pressure, respectively, within one single respiratory cycle. Notably, during one single respiratory cycle the heart usually beats several times. For example, if the heart beats six times during one respiratory cycle, $PP_{max}$ and $PP_{min}$ for six heart beats may be measured. To calculate the pulse pressure variation, the single maximum pulse pressure value and the single minimum pulse pressure value for the entire sequence of six subsequent heart beats have to be determined.

Adversely, both previously described approaches for determining an indicator representative for volume responsiveness, i.e. the SPV-approach and PPV-approach, strictly require to reliably measure blood pressure values associated with each individual heart beat in the course of the detection period, e.g. during one respiratory cycle comprising approximately six heart beats. However, due to frequently occurring artefacts or arrhythmias of the heart, not all of the measured values actually reflect the patient's heart-lung interaction in terms of volume responsiveness. This phenomenon makes both above approaches prone to errors. In fact, analysis of the respiratory changes in arterial pressure is hardly possible in patients with cardiac arrhythmias.

A well-known and convenient way to determine the arterial blood pressure of a patient is to use the so-called "oscillometric non-invasive blood pressure measurement method". By that method, the pressure in a pressure cuff, which is usually applied to the patient's arm, is continuously increased or decreased. For example, the pressure in the pressure cuff may be initially set to a value well above the systolic pressure of the patient, and may then be continuously decreased to a value below the diastolic pressure of the patient. Hereby, the pressure in the pressure cuff is continuously decreased over a time period which corresponds to a plurality of heart beats. A manometer is connected to the pressure cuff which not only indicates the continuously decreasing pressure applied to the pressure cuff, but, in addition (due to the principle action=reaction) also indicates the pressure oscillation based on the varying pulse signal, i.e. pulse amplitude and waveform. Further, the corresponding result of a single heart beat in any artery sensed by any method will be called a "pulse". By plotting exclusively such cyclic pressure variations, i.e. oscillations, indicated by the manometer over the time, the oscillation amplitude is not constant but rather bell shaped. The maximum oscillation is usually reached when the pressure applied to the pressure cuff is somewhere in the middle between the systolic and the diastolic pressure of the patient. In other words, the sensitivity of the manometer with respect to the pressure oscillations caused by the heart beats is at its maximum whenever the cuff pressure substantially corresponds to an intermediate value between the systolic and the diastolic pressure (or is slightly below that intermediate value).

A pressure cuff being connected to a manometer is schematically shown in FIG. 3. The pressure cuff is applied to a patient's arm and indirectly, through skin, fat, muscles and inter-connective tissue, exerts pressure on an artery. An electrocardiogram (ECG) signal over the time is schematically shown in FIG. 4a. The pressure in the pressure cuff that is detected as a function of time by the manometer is schematically shown in FIG. 4b. The plotted pressure signals in FIG. 4b represent superposition of the continuously decreasing pressure applied to the pressure cuff on one hand, and cyclic pressure oscillations caused by the pulses of the patient on the other hand. In this example, the pressure in the pressure cuff is continuously decreased from a value above the systolic pressure $P_{sys}$ of the patient to a value below the diastolic pressure $P_{dia}$ of the patient, e.g. via a not shown valve. Notably, instead of continuously decreasing the pressure in the pressure cuff, it is also possible to continuously increase the pressure in the pressure cuff. By another plot, exclusively the pressure oscillations detected by the manometer are schematically illustrated in FIG. 4c. These pressure oscillations are illustrated as oscillating around an average value. As can be seen from FIG. 4c, the amplitude of the pressure oscillations is not constant but has a maximum when the pressure in the pressure cuff substantially corresponds to the 50% intermediate value between the systolic blood pressure and the diastolic blood pressure of the patient.

As noted previously, by the above described oscillometric non-invasive blood pressure measurement method, the cuff pressure is continuously increased or decreased. Accordingly, no constant measurement conditions can be applied and, thus, this method only allows for determining a single systolic pressure value and a single diastolic pressure value. A reliable determination of the individual systolic and diastolic pressure values associated with each single individual heart beat cannot be provided by that blood pressure measuring approach. Consequently, such an approach does not reliably allow for determining the volume responsiveness of the patient via the SPV-approach or the PPV-approach.

EP 0 078 090 A1 teaches a non-invasive blood pressure measurement method that allows for determining pulse pressure variation. According to this method, a fluid-filled pressure cuff is permanently attached to a patient's finger. A light source and a light detector are integrated in the pressure cuff, the light source and the light detector forming part of a photo-electric plethysmograph. The cuff pressure is controlled—via an electric pressure valve—by the plethysmographic signal in closed-loop operation, so that the arterial volume in the finger is maintained at a value to be pre-adjusted. Measuring the pressure in the pressure cuff, thus, allows for determining the arterial blood pressure of the patient.

However, permanently pressing the sensors to the patient's finger negatively affects blood circulation and can cause severe tissue damage or even necrosis of the finger. Furthermore, the finger is relatively remote from the patient's heart, and the diameter of arterial vessels in the finger is relatively small compared to the diameter of arterial vessels close to the heart. Due to interference effects caused by pressure reflections occurring when the diameter of arterial vessels abruptly changes, e.g. when arterial vessels branch, the blood pressure wave form measurable at the finger only imprecisely corresponds to the arterial blood pressure of interest, namely the central arterial blood pressure and waveform closest to the patient's heart.

It is therefore an object of the present disclosure to provide a simple and robust method or means for reliably determining an indicator representative for the patient's volume responsiveness. In particular, it is an object of the present disclosure to provide a method or means for determining volume responsiveness of a patient, which method or means minimizes the negative impact (exerted e.g. by artefacts or arrhythmias of the patient's heart) on the indicator to be determined. The method or means according to the present disclosure should preferably also reliably be implemented on the basis of oscillometric non-invasive blood pressure measurement methods known in the art.

SUMMARY

It is believed that these objects may be achieved in some instances by the method according to the present disclosure and claims. Advantageous features of the method are described in the dependent claims.

In some arrangements, the present disclosure refers to a method of determining an indicator that is representative for a patient's volume responsiveness, including the following steps:

(i) measuring a sequence of pulse signals of a patient;
(ii) determining an envelope(signal)-curve based on the sequence of measured pulse signals;
(iii) determining a fit(envelope(signal))-function based on the previously determined envelope(signal)-curve, the fit(envelope(signal))-function representing an idealised curve progression of the envelope(signal)-curve without comprising pulse variations caused by ventilation or respiration induced heart-lung interaction;
(iv) determining respiratory pulse variation signals corresponding to the pulse variations caused by ventilation or respiration induced heart-lung interaction;
(v) determining an envelope(respiration)-curve based on the previously determined respiratory pulse variation signals;
(vi) determining a fit(envelope(respiration))-function based on the previously determined envelope(respiration)-curve, the fit(envelope(respiration))-function representing an idealised curve progression of the envelope(respiration)-curve;
(vii) determining the indicator that is representative for the patient's volume responsiveness based on the fit(envelope(signal))-function and the fit(envelope(respiration))-function.

The first (optional) step of the method according to the present disclosure corresponds to data acquisition, namely measuring a sequence of pulse signals of a patient, e.g. signals corresponding to blood pulsations from continuous or semi-continuous recordings of pressure, flow, Doppler-ultrasound, photo-plethysmographic, contrast agent x-ray, rapid or high speed isotope radiation scan, rapid or high-speed CT-scan, rapid or high-speed magnetic resonance tomography, rapid or high-speed photon emission tomography, signals, and any combination thereof, et cetera. Notably, this method step is not essential for successfully applying the present disclosure. It is evident that a sequence of pulse signals of a patient may have been measured previously, e.g. by a physician. The measured pulse signals may hereafter have been stored. These data may be used by the method of the present disclosure such that the present disclosure may alternatively immediately start with the second method step (using the stored measured pulse signals).

How to measure pulse signals of a patient is well known to those skilled in the art. There are various established methods for doing so, including direct or invasive blood pressure measurement methods and indirect or non-invasive blood pressure measurement methods, and see other methods to record any arterial pulsation signals above.

Preferably, the oscillometric non-invasive blood pressure measurement method as described above in view of FIGS. 3, 4a, 4b, and 4c is used. This blood pressure measurement method is well-known and convenient to apply for data acquisition. It has the advantage, compared to other blood pressure methods, such as invasive blood pressure methods, that it does not imply any adverse effects on the patient which are associated with alternative invasive blood pressure measurement approaches, e.g. local and/or bloodstream infections, thromboembolic complications, bleedings et cetera.

The sequence of measured pulse signals may be detected over a time period of between e.g. 10 seconds and four minutes, preferable of between 30 seconds and two minutes, more preferably of about one minute to safely cover at least four respiratory cycles. The pulse rate of the patient depends on various factors, such as age, stress, etc. The heart of an adult beats usually between 50 to 90 times per minute. Thus, a comparatively larger number of pulse variations caused by heart beats can be detected in the detection time period. Such an approach is advantageous in view of the data quality underlying the calculation of the indicator representative for the patient's volume responsiveness according to the present disclosure. However, when applying the oscillometric non-invasive blood pressure measurement method, the detection period should preferably not exceed three minutes so as to avoid adverse effects due to disturbed blood flow caused by the pressure of the pressure cuff.

Furthermore, the detection time period should cover at least one full respiration respectively, ventilation cycle. Preferably, however, the sequence of measured pulse signals is detected over a time period corresponding to a plurality of subsequent respiratory or ventilator cycles of the patient. For example, the detection time period may correspond to between two and ten subsequent respiratory cycles. As described above, it is well known that the patient's respiration has a detectable influence on pulse variation. While the measured variation of the blood pressure is primarily derived from the function of the heart, i.e. from its cyclic contractions and relaxations, there is also another influential factor to be considered: Thus, two functions are superimposed: Variations of higher frequency caused by the function of the heart are superimposed by variations of lower frequency caused by the respiration or ventilation of the patient. Notably, such low frequency variations caused by the patient's respiration are not only detected with mechanically ventilated patients, but also with non-ventilated patients breathing spontaneously. Even though the effect of spontaneous breathing is somehow similar to the effect of mechanical ventilation as to variations of blood pressure, both effects are actually not the same for the following reason: In the case of mechanical ventilation, air is pressed at high pressure from outside into the lungs during inspiration, whereas, in case of spontaneous breathing, air is sucked by lower pressure into the lungs during inspiration. Irrespective of these phenomenological distinctions, the method according to the present disclosure can be equally applied to mechanical ventilated and spontaneous breathing non-ventilated patients, provided that the respiration—or ventilation—induced maneuver produces significant heart-lung-interaction. Only the resulting indicator representative for the patient's volume responsiveness has to be interpreted reasonably along other characteristics of each single patient. Data interpretation, however, falls within the expert knowledge of any physician or other medically trained person who carries out the diagnosis.

As known in the art, the measured pulse signals are preferably represented as a signal curve oscillating around an average value of the measured signals. Furthermore, the measured pulse signals may be represented as a function over time or, alternatively, as a function over the clamping pressure exerted by the pressure cuff, if the oscillometric non-invasive blood pressure measurement method is used, wherein the pressure applied in the pressure cuff is continuously increased or decreased in the course of the measurement period.

As a second step of the method according to the present disclosure, an envelope(signal)-curve based on the sequence of measured pulse signals is determined. Usually, an envelope curve or function of a rapidly varying signal is considered to be a smooth curve outlining the extremes in amplitude of the rapidly varying signal. For example, the envelope curve or function may be determined by simply connecting the maxima (and the minima) of the rapidly varying signal. However, according to the present disclosure, the envelope curve of the blood pressure signals, i.e. the envelope(signal)-curve, is preferably determined by continuously determining a distance dimension of the measured pulse signals from an average thereof and, thereafter, by preferably applying a low pass filter to the distance dimension. Preferably, the low pass filter has a cutoff frequency below the pulse rate of the patient. For example, the portion below the average value of the oscillating curve of measured pulse signals is preferably folded up to the upper portion. Then, the resulting curve is preferably flattened by using a low pass filter having a cutoff frequency below the pulse rate of the patient. Preferably, the resulting curve is flattened in such a way that the area below the (flattened) curve remains unchanged as compared to the area under the non-flattened curve. Optionally, the flattened curve may additionally be multiplied by a predetermined value. If the flattened curve is multiplied, for example, by the square root of 2 ($\sqrt{2}$), the finally obtained envelope(signal)-curve substantially is at the level of the upper extremes in amplitude of the measured pulse signals.

Alternatively, the distance dimension could be defined as the squared signal or the extreme values within a certain region, e.g. of about one pulse width or any other metric function. In case of using the absolute value of the difference as a distance dimension, the result correlates best with the Stroke Volume Variation (SVV), which is another well known parameter for volume responsiveness. With the absolute value of the difference to the power of n as a distance dimension, the result correlates better to Pulse Pressure Variation (PPV) with raising n. With the maximum metric, i.e. with infinite n as a distance dimension, the result correlates best with PPV. For example, the maximum metric could be realized by searching the maximum value minus the minimum value of the difference within a moving window equal to the duration of a heart beat.

The average value (used as the basis of the distance dimension calculation) of the measured pulse signals can be determined as moving average over a period of one single pulse cycle of the patient. Given a series of numbers (in this case: the measured pulse signals) and a fixed subset size (in this case: the period of one single pulse cycle of the patient), the first element of the moving average is obtained by taking the average of the initial fixed subset of the number series. Then the subset is modified by "shifting forward", that is excluding the first number of the series and including the next number following the original subset in the series. This creates a new subset of numbers, which is averaged. This process is repeated over the entire data series.

In some instances, it may be advantageous, in order to obtain a well fittable envelope(signal)-curve, to apply a window function to the measured pulse signals before determining the envelope(signal)-curve. In particular, if the pulse signals are measured using a continuous invasive blood pressure measurement method, application of a window function is advantageous. Unlike the above-described oscillometric non-invasive blood pressure measurement method, pulse signals measured by a continuous invasive blood pressure measurement method usually do not exhibit any bell-shaped form. On the other hand, if pulse signals are measured using an oscillometric non-invasive blood pressure measurement method, application of a window function may not be required. Under such circumstances, measured pulse signals already exhibit a bell-shaped form, and, therefore, are—as such—well fittable with a functional prototype also exhibiting a bell-shaped form.

If a window function is applied, the window function is preferably a non-negative smooth bell-shaped curve, for example a Cauchy-Lorentz function.

As a third step of the method according to the disclosure, a fit(envelope(signal))-function is determined based on the previously determined envelope(signal)-curve. The fit(envelope(signal))-function represents an idealised curve progression of the envelope(signal)-curve with the object to exclude any pulse variation caused by ventilation or respiration induced heart-lung interaction.

Preferably, the fit(envelope(signal))-function is determined based on a predetermined functional prototype. More preferably, the functional prototype is a non-negative smooth bell-shaped curve, for example a Cauchy-Lorentz function. If the measured pulse signals are plotted over time t, such a functional prototype may be defined as follows:

$$f(t) = \frac{f_{amp}}{1 + \left(\frac{t - f_{max}}{f_{bw}}\right)^2}$$

Notably, if the oscillometric non-invasive blood pressure measurement method with continuously increasing or decreasing cuff pressure p is applied, and if the measured pulse signals are plotted as a function of the cuff pressure, the functional prototype may also be defined as follows:

$$f(p) = \frac{f_{amp}}{1 + \left(\frac{p - f_{max}}{f_{bw}}\right)^2}$$

The functional prototype preferably comprises at least one parameter, and even more preferably at least two parameters, that is/are selected so as to achieve an optimum fitting of the fit(envelope(signal))-function to the envelope(signal)-curve. In the above example, there are three parameters that can be freely selected, namely $f_{amp}$, $f_{max}$, and $f_{bw}$. The parameter $f_{amp}$ is decisive for the amplitude of the bell-shaped curve of the functional prototype. The parameter $f_{max}$ is decisive for the location of the maximum on the time-axis or pressure-axis, while the parameter $f_{bw}$ is decisive for the width at half maximum.

The at least one parameter (e.g. amongst the above three parameters) can be selected by any known optimization algorithm, for example an optimization algorithm based on the smallest error squares. Preferably, the Levenberg-Marquardt algorithm is used to select the at least one parameter of the functional prototype. In the above example, one, two or preferably all three parameters may be optimized.

The difference between the envelope(signal)-curve and the fit(envelope(signal))-function reflects a modulation which is due to the respiration or ventilation of the patient. Thus, as the fourth step of the method, respiratory pulse variation signals corresponding to the pulse variations caused by the respiration of the patient are determined. Preferably, the respiratory pulse variation signals are determined in such a way that the respiratory pulse variation signals oscillate around an average value thereof. Preferably, the area defined by the lower part of the curve of the respiratory pulse variation signals (i.e. the area below the average value) substantially corresponds to the area defined by the upper part of the curve of the respiratory pulse variation signals (i.e. the area above the average value).

To determine the average value of the respiratory pulse variation signals, a low pass filter may be applied to the envelope(signal)-curve, the low pass filter preferably having a cutoff frequency below the respiratory frequency of the patient. To obtain respiratory pulse variation signals, the above mentioned average value has to be subtracted from the envelope(signal)-curve. Thus, respiratory pulse variation signals can be easily represented as a curve oscillating around the average value.

Next, as a fifth step of the method according to the disclosure, an envelope(respiration)-curve is determined based on the previously determined respiratory pulse variation signals.

Preferably, the fifth step is carried out by substantially the same approach as the second step of the method of the present disclosure. Consequently, the envelope(respiration)-curve, is preferably calculated by continuously determining a distance dimension of the respiratory pulse variation signals from an average thereof and by thereafter preferably applying a low pass filter to the distance dimension. Preferably, the low pass filter has a cutoff frequency below the respiration frequency of the patient. In other words, the portion below the average value of the oscillating curve of respiratory pulse variation signals is preferably folded up to the upper portion. Then, the resulting curve is preferably flattened by using a low pass filter having a cutoff frequency below the respiration frequency of the patient. Preferably, the curve is flattened in such a way that the area below the (flattened) curve remains unchanged as compared to the area under the non-flattened curve. Optionally, the flattened curve may additionally be multiplied by a predetermined value. If the flattened curve is multiplied, for example, with the value of the square root of 2 ($\sqrt{2}$), the finally obtained envelope (respiration)-curve substantially is at the level of the upper extremes in amplitude of the respiratory pulse variation signals.

Preferably, the average value (used as the basis of the distance dimension calculation) of the respiratory pulse variation signals is determined as moving average over a period of one single respiration cycle of the patient.

As a sixth step of the method according to the disclosure, a fit(envelope(respiration))-function is determined based on the previously determined envelope(respiration)-curve. The fit(envelope(respiration))-function represents an idealised curve progression of the envelope(respiration)-curve. Preferably, the sixth step is carried out by substantially the same approach as the third step of the method of the present disclosure.

Consequently, the fit(envelope(respiration))-function is preferably determined based on a predetermined functional prototype. More preferably, the functional prototype is a non-negative smooth bell-shaped curve, for example a Cauchy-Lorentz function. If the respiratory pulse variation signals are plotted over time t, such a functional prototype may be defined as follows:

$$g(t) = \frac{g_{amp}}{1 + \left(\frac{t - g_{max}}{g_{bw}}\right)^2}$$

Notably, if the oscillometric non-invasive blood pressure measurement method with continuously increasing or decreasing cuff pressure p is applied, and if the respiratory pulse variation signals are plotted as a function of the cuff pressure, the functional prototype may similarly be defined as follows:

$$g(p) = \frac{g_{amp}}{1 + \left(\frac{p - g_{max}}{g_{bw}}\right)^2}$$

The functional prototype preferably comprises at least one parameter, and even more preferably at least two parameters, that is/are selected so as to achieve an optimum fitting of the fit(envelope(respiration))-function to the envelope(respiration)-curve. In the above example, there are three parameters that can be freely selected, namely $g_{amp}$, $g_{max}$, and $g_{bw}$. The parameter $g_{amp}$ is decisive for the amplitude of the bell-shaped curve of the functional prototype; the parameter $g_{max}$ is decisive for the location of the maximum on the time-axis or pressure-axis; and the parameter $g_{bw}$ is decisive for the width at half maximum.

The at least one parameter (e.g. amongst the above three parameters) can be selected by any known optimization algorithm, for example an optimization algorithm based on the smallest error squares. Preferably, the Levenberg-Marquardt algorithm is used to accordingly select the at least one parameter of the functional prototype. In the above example, one, two or preferably all three parameters may be optimized.

Preferably, (in order to avoid any bias from the calculatory steps involved) the envelope(respiration)-curve and the fit(envelope(respiration))-function are calculated analogously to the envelope(signal)-curve and the fit(envelope(signal))-function, respectively, but represent the respiratory pulse variation signals instead of the measured pulse signals. That is, for example, if the Cauchy-Lorentz function is used as functional prototype to determine the fit(envelope(signal))-function, also the Cauchy-Lorentz function is preferably used as functional prototype to determine the fit(envelope(respiration))-function.

Finally, in the seventh step of the method of the present disclosure, the indicator that is representative for the patient's volume responsiveness is determined based on the fit(envelope(signal))-function and the fit(envelope(respiration))-function. Preferably, the indicator that is representative for the patient's volume responsiveness is determined based on at least one parameter of the fit(envelope(signal))-function and at least one parameter of the fit(envelope(respiration))-function.

For example, the indicator that is representative for the patient's volume responsiveness can be determined based on a ratio between a maximum of the fit(envelope(signal))-function and a maximum of the fit(envelope(respiration))-function.

It was found that such a ratio represents an appropriate indicator that is representative for the patient's volume responsiveness. For example, if a Cauchy-Lorentz function is used as functional prototype to determine both, the fit(envelope(signal))-function and the fit(envelope(respiration))-function, then the ratio that is representative for the patient's volume responsiveness VR can be determined as follows:

$$VR = \frac{g_{amp}}{f_{amp}} * 100\%$$

As described above, it was known in the art that pulse variations caused by respiration or ventilation induced heart-lung-interaction of a patient can be used to predict volume responsiveness of that patient. The indicator obtained by the method according to the disclosure serves a similar purpose as the "pulse pressure variation-indicator" known from the prior art.

However, unlike the methods for determining volume responsiveness known in the art, the method according to the disclosure does not require to rely on single maximum/minimum blood pressure values corresponding to one single heart beat. Such prior art methods may lead to questionable results due to deviations occurring either within the single heart beat and/or the rhythm of successive beats. Instead, the complete sequence (suite) of measured pulse signals (e.g. of several respiratory cycles) is taken into account by the method for determining the indicator that is representative for the patient's volume responsiveness. Thus, even if any artefacts or arrhythmias of the heart occur and are recorded, their impact on the result according to the present disclosure is negligible. For example, if the pulse signals are measured over a period of 60 heart beats, any single artefact recorded for these 60 heart beats does not influence the result of the method according to the present disclosure. In contrast, such an artefact will readily lead to completely false results when using the methods known in the prior art. Erroneous results, however, may lead to inappropriate or even life-threatening decisions by the physician, e.g. interpreting falsely high pulse variations as significant cardiac volume responsiveness and subsequently administering fluid to a patient who is not in need thereof.

The curves of non-invasive blood pressure signals are distorted in a non-linear fashion depending on the clamping pressure of the pressure cuff. That is why the maximum of the fit(envelope(respiration))-function is shifted as compared to the maximum of the fit(envelope(signal))-function. Accordingly, it would have been expected that such a distortion resulting in phase shifts would not allow such data to be used for the provision of a reliable indicator being representative for a patient's volume responsiveness. However, it is the merit of the inventors to have found out that the method according to the present disclosure perfectly reflects the patient's physiological status. It was found that—irrespective of such phase shifts—the ratio of the amplitudes is a reliable and predictive indicator of the patient's volume responsiveness.

The indicator (e.g. the ratio VR) obtained by the method according to the disclosure supports the physician's decision as to how to treat the patient. However, the indicator does not provide a therapeutic guideline for the physician. Rather, the indicator needs to be aligned with a multitude of other diagnostic information to arrive at the appropriate therapeutic treatment. For example, the physician may decide on the basis of his experience and other diagnostic information for an individual patient that, for an individual patient mechanically ventilated at a tidal volume of 8 ml/kg predicted body weight, a ratio VR of e.g. greater than 12% indicates the intervention threshold that particular patient may have a relatively high volume responsiveness and that fluid should be administered to increase cardiac output and, thus, to optimize tissue perfusion, without evoking a fluid overload in the patient's circulation.

Notably, it is also possible to calculate systolic blood pressure values and diastolic blood pressure values based on the selected fit parameters of the fit(envelope(signal))-function. The formulas depend on the arrangement of the used measuring assembly and can be empirically determined using multiple regression.

Notably, as will be apparent to those skilled in the art, method steps (ii) and (iii) of the method according to the present disclosure might be carried out simultaneously. That is, by applying a corresponding algorithm which integrally comprises both method steps, i.e. method step (ii) and method step (iii), it is possible to directly (i.e. in just one method step) calculate the fit(envelope(signal))-function based on the measured sequence of pulse signals.

Similarly, as will be apparent to those skilled in the art, method steps (v) and (vi) of the method according to the present disclosure might be carried out simultaneously. That is, by applying a corresponding algorithm which integrally comprises both method steps, i.e. method step (v) and method step (vi), it is possible to directly (i.e. in just one method step) calculate the fit(envelope(respiration))-function based on the previously determined respiratory pulse variation signals.

According to another aspect, the disclosure also refers to a logic unit for determining an indicator that is representative for a patient's volume responsiveness, configured to carry out the following steps:
  determining an envelope(signal)-curve based on a sequence of previously measured pulse signals;
  determining a fit(envelope(signal))-function based on the previously determined envelope(signal)-curve, the fit(envelope(signal))-function representing an idealised curve progression of the envelope(signal)-curve without comprising pulse variations caused by respiration of the patient;
  determining respiratory pulse variation signals corresponding to the pulse variations caused by the respiration of the patient;
  determining an envelope(respiration)-curve based on the previously determined respiratory pulse variation signals;
  determining a fit(envelope(respiration))-function based on the previously determined envelope(respiration)-curve, the fit(envelope(respiration))-function representing an idealised curve progression of the envelope (respiration)-curve;
  determining the indicator that is representative for the patient's volume responsiveness based on the fit(envelope(signal))-function and the fit(envelope(respiration))-function.

According to yet another aspect, the disclosure also refers to a system for determining an indicator that is representative for a patient's volume responsiveness, comprising the above described logic unit and a blood pressure measurement device, the blood pressure measurement device being configured for measuring a sequence of pulse signals of a patient, wherein the system is configured for providing the pulse signals measured e.g. by the blood pressure measurement device as input values to the logic unit.

Preferably, the blood pressure measurement device comprises a pressure cuff that may be configured for being disposed around a patient's arm so as to measure the patient's arterial blood pressure in a non-invasive way.

The blood pressure measurement device is preferably adapted to carry out the previously described method according to the present disclosure.

A preferred example of an embodiment of the method according to the disclosure is illustrated with reference to the following figures.

DETAILED DESCRIPTION

In a preferred method according to the disclosure, in the first step, pulse signals of a patient are measured. Preferably, the pulse signals are measured using the oscillometric non-invasive blood pressure measurement method, which method can easily be carried out without adversely affecting the patient. The oscillometric non-invasive blood pressure measurement method, as described above in view of the schematic representations shown in FIGS. 3, 4a, 4b, and 4c, is well known in the art. Notably, other pulse measurement methods may equally be applied to measure the patient's pulse.

Figure 1:
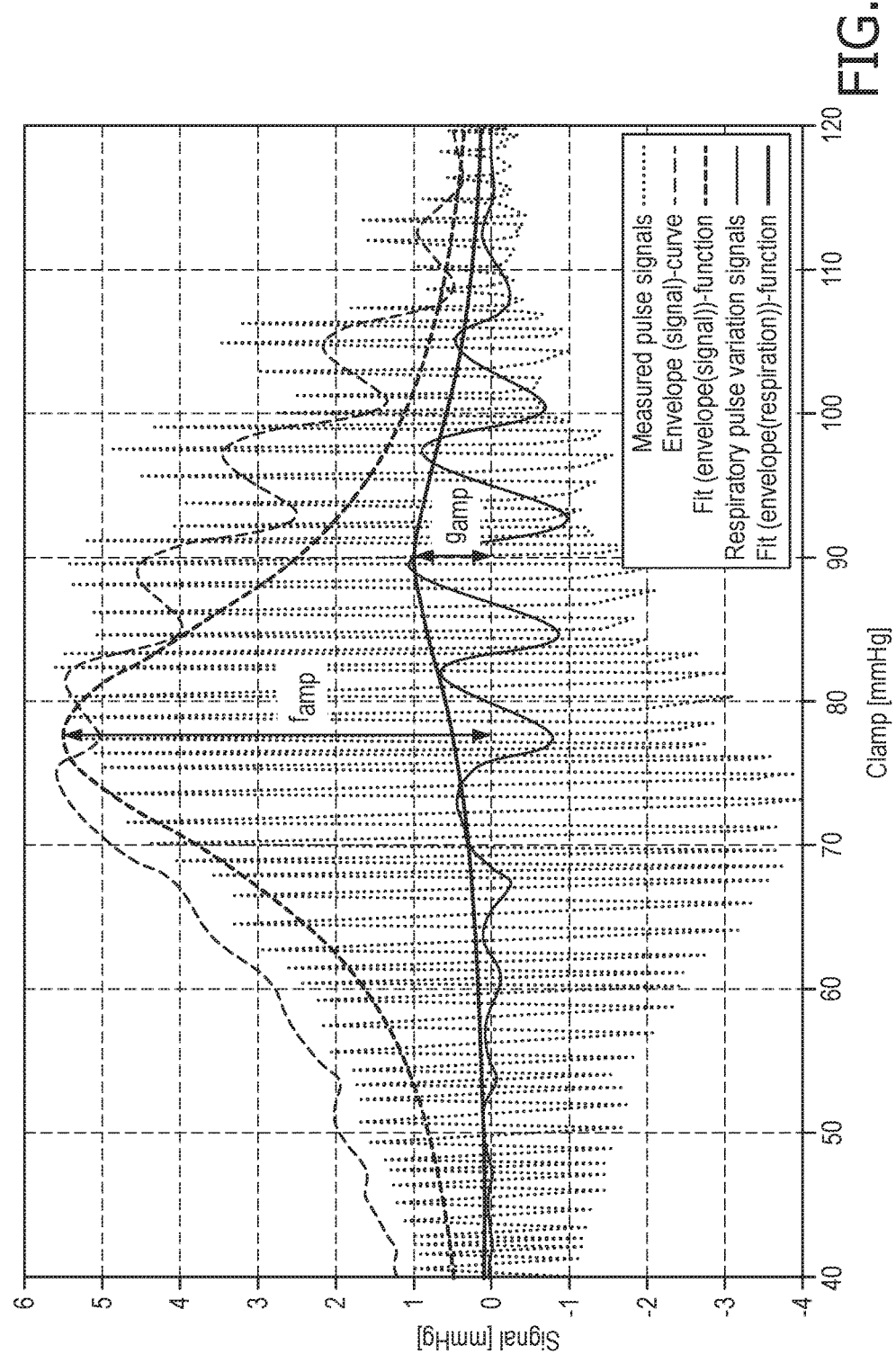
FIG. 1 is a diagram displaying the measured pulse signals, the envelope(signal)-curve, the fit(envelope(signal))-function, the respiratory pulse variation signals, and the fit (envelope(respiration))-function, all of them determined according to the method of the present disclosure.

Similar to the curve described above in view of FIG. 4c, the measured pulse signals are represented in FIG. 1 as a curve (dotted line) oscillating around an average value thereof. The average value may preferably be determined as moving average over a period of one pulse cycle of the patient. In this example, the pressure applied to the pressure cuff is continuously increased from about 40 mmHg to about 120 mmHg at a substantially constant rate. Thus, it is possible to represent the oscillating measured pulse signals as a function over the clamping pressure being constantly increased over time. As a matter of fact, a representation as a function over the time may be equally displayed. By the example shown in FIG. 1, the pressure is increased from about 40 mmHg to about 120 mmHg within a detection time period of about one minute. Thus, in this example, about 60 heart beats and about ten respiratory cycles of a patient are captured within the detection time period.

Next, as the second step of the method, the envelope (signal)-curve is determined. In this example, the envelope (signal)-curve is determined by continuously determining a distance dimension of the measured pulse signals from the average value thereof and by then applying a low pass filter to the distance dimension. The low pass filter has a cutoff frequency below the pulse rate of the patient. In other words, the portion below the average value of the oscillating curve of measured pulse signals is folded up to the upper portion, so as to obtain exclusively positive pressure values. Then, the resulting curve is flattened by using the low pass filter with a cutoff frequency below the pulse rate of the patient. Thereby, the curve is flattened in such a way that the area below the curve remains substantially unchanged. In the present example, the flattened curve is then multiplied by ($\sqrt{2}$), so that the finally obtained envelope(signal)-curve is essentially positioned at the level of the upper extremes in amplitude of the measured pulse signals.

As can be seen from FIG. 1, the envelope(signal)-curve (light dashed line) is modulated by another influential factor (i.e. the patient's respiration or ventilation) which has an impact on the measured blood pressure signals. In contrast, the high frequency variation of the pulses, caused by the patient's heart beats, has been filtered out by the manipulation according to the second step of the disclosure.

Next, in the third step of the method, a fit(envelope (signal))-function is determined (dark dashed line in FIG. 1) using a functional prototype. The functional prototype chosen in this example is a non-negative smooth bell-shaped curve, namely a Cauchy-Lorentz function, exhibiting the following generic formula:

$$f(p) = \frac{f_{amp}}{1 + \left(\frac{p - f_{max}}{f_{bw}}\right)^2}$$

Thus, there are three parameters that can be freely selected to fit the functional prototype to the envelope (signal)-curve, namely $f_{amp}$, $f_{max}$, and $f_{bw}$. The parameter $f_{amp}$ is decisive for the amplitude of the bell-shaped curve of the functional prototype; the parameter $f_{max}$ is decisive for the location of the maximum on the pressure-axis; and the parameter $f_{bw}$ is decisive for the width at half maximum of the bell-shaped curve.

In this example, the Levenberg-Marquardt algorithm, which is known to those skilled in the art, is applied as optimization algorithm to identify values for the parameters $f_{amp}$, $f_{max}$, and $f_{bw}$ that lead to the best fitting of the fit(envelope(signal))-function to the envelope(signal)-curve. However, other known optimization algorithms may equally be applied for that fitting step.

Then, by the fourth step of the method according to the disclosure, the respiratory pulse variation signals are determined which substantially correspond to the difference between the envelope(signal)-curve and the fit(envelope (signal))-function. The respiratory pulse variation signals are determined in such a way that the respiratory pulse variation signals oscillate around an average value thereof. Preferably, a low pass filter is applied to the envelope (signal)-curve to determine the average value of the respiratory pulse variation signals, the low pass filter having a cutoff frequency below the respiratory frequency of the patient. To obtain respiratory pulse variation signals, the above mentioned average value has to be subtracted from the envelope(signal)-curve. Thus, an oscillating curve, similar to the curve of the measured pulse signals, is obtained, but having a lower oscillating frequency which is caused only by the patient's respiration.

As the fifth and sixth step of the method according to the disclosure, an envelope(respiration)-curve and a fit(envelope(respiration))-function are determined. This is done substantially the same way in which the envelope(signal)-curve and the fit(envelope(signal))-function have been previously determined in method steps 2 and 3, respectively. Notably, in FIG. 1, only the fit(envelope(signal))-function is shown (dark line), but not the envelope(signal)-curve.

As fifth step of the method, the envelope(respiration)-curve is determined. As before, the envelope(respiration)-curve is determined by continuously determining a distance dimension of the respiratory pulse variation signals from the average value thereof and by then applying a low pass filter to the distance dimension. The low pass filter has a cutoff frequency below the respiration frequency of the patient. In other words, the portion below the average value of the oscillating curve of respiratory pulse variation signals is folded up to the upper portion, so as to obtain exclusively positive pressure values. Then, the resulting curve is flattened by using the low pass filter with a cutoff frequency below the respiration frequency of the patient. Thereby, the curve is flattened in such a way that the area below the curve remains substantially unchanged. In the present example, the flattened curve is then multiplied by the value of $\sqrt{2}$, so that the finally obtained envelope(respiration)-curve is essentially positioned at the level of the upper extremes in amplitude of the respiratory pulse variation signals.

Next, in the sixth step of the method, a fit(envelope(respiration))-function is determined using a functional prototype. The same functional prototype as before is chosen, namely the Cauchy-Lorentz function, exhibiting the following generic formula:

$$g(p) = \frac{g_{amp}}{1 + \left(\frac{p - g_{max}}{g_{bw}}\right)^2}$$

Thus, there are again three parameters that can be freely selected to fit the functional prototype to the envelope (respiration)-curve, namely $g_{amp}$, $g_{max}$, and $g_{bw}$. The parameter $g_{amp}$ is decisive for the amplitude of the bell-shaped curve of the functional prototype; the parameter $g_{max}$ is decisive for the location of the maximum on the pressure-axis; and the parameter $g_{bw}$ is decisive for the width at half maximum of the bell-shaped curve.

In this example, again the Levenberg-Marquardt algorithm is applied as optimization algorithm to find those parameters $g_{amp}$, $g_{max}$, and $g_{bw}$ that lead to the best fitting of the fit(envelope(respiration))-function to the envelope(respiration)-curve.

Finally, in the seventh step of the method according to the present disclosure, the indicator VR for the patient's volume responsiveness is determined, i.e. by calculating the ratio of the previously identified parameters $g_{amp}$ and $f_{amp}$ of the corresponding functional prototypes.

Figure 2:
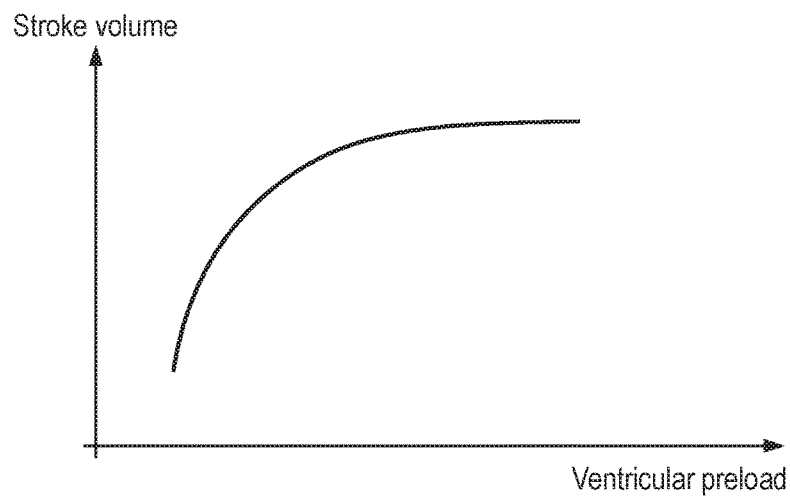
FIG. 2 is a schematic representation of the so-called "Frank-Staring-curve"
Figure 3:
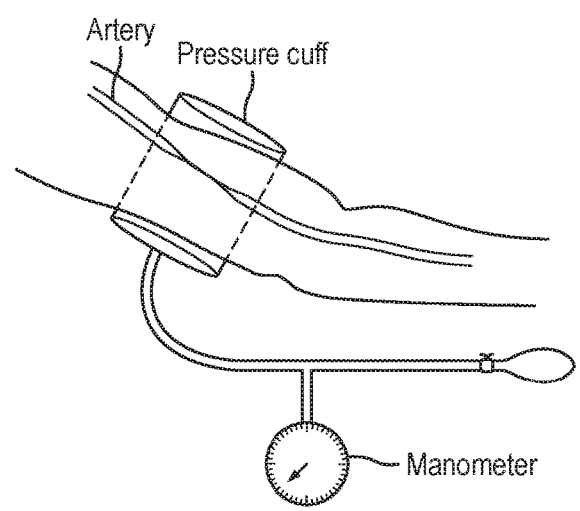
FIG. 3 is a schematic representation of a typical configuration used in the oscillometric non-invasive blood pressure measurement method.
Figure 4A:
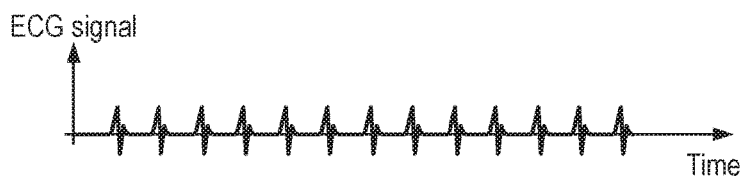
FIG. 4a is a schematic representation of heart beat signals detected by an electrocardiogram over the time.
Figure 4B:
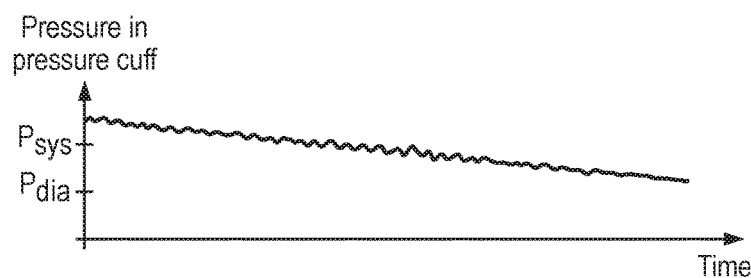
FIG. 4b is a schematic representation of the pressure measured by a manometer in the oscillometric non-invasive blood pressure measurement method.
Figure 4C:
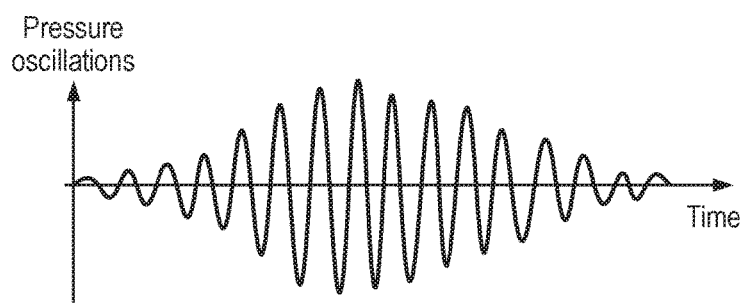
FIG. 4c is a schematic representation of only the pressure oscillations measured by the manometer in the oscillometric non-invasive blood pressure measurement method.

As set forth above, it is known in the art that respiration or ventilation of a patient has an impact on his pulse pressure. That is, variations of arterial pulse can be detected, which variations have a frequency corresponding to the respiration frequency. The magnitude of these pulse variations substantially depends on the patient's heart's position on the Frank-Starling curve (as schematically illustrated in FIG. 2). If the magnitude of the pulse variations caused by the patient's respiration is relatively large, the patient is supposed to be on the steep part of the Frank-Starling curve, which means that the patient exhibits relatively "good" volume responsiveness. To the contrary, if the magnitude of the pulse variations caused by the patient's respiration is relatively small, the patient is supposed to be on the flat part of the Frank-Starling curve, which means that the patient exhibits relatively "bad" or no volume responsiveness. The magnitude of the pulse variations caused by the patient's respiration is represented by the parameter $g_{amp}$ in the above example of the method. Similar to the calculation of the pulse pressure variation (PPV) as indicator for the patient's volume responsiveness, the parameter $g_{amp}$ is "normalized". That is, $g_{amp}$ is divided it by the magnitude $f_{amp}$ of the pulse variations caused by heart beats. Therefore, the indicator VR obtained according to the present disclosure is similar to the pulse pressure variation (PPV) as indicator for the patient's volume responsiveness known in the art.

However, the method according to the present disclosure—unlike the methods known in the art—does not rely on single maximum/minimum values of measured pulse pressure variations corresponding to one single heart beat. Instead, the method according to the present disclosure takes all pulse signals measured within the detection period into account. Therefore, bias by any artefacts or arrhythmias of the heart occurring within the detection period, is avoided by the method according to the present disclosure. Accordingly, the physician is provided with highly reliable information by the present method which allows him (in combination with further information of the patient's status) to make a well-founded decision as to the patient's volume responsiveness.

Summarizing the above, the present disclosure provides a simple and robust method (and means) for reliably determining an indicator representative for the patient's volume responsiveness. Moreover, the method (or means) can be easily and reliably implemented on the basis of the oscillometric non-invasive blood pressure measurement method known in the art.

The invention claimed is:

1. Method of determining administration of a fluid to a patient based on an indicator representative of the patient's volume responsiveness, comprising the following steps:
   (i) measuring a sequence of pulse signals of the patient over a time period corresponding to a plurality of subsequent respiratory cycles of the patient, wherein the sequence of measured pulse signals is detected by an oscillometric non-invasive pulse measurement method using a pressure cuff, wherein the pressure applied in the pressure cuff is continuously increased or decreased in the course of a measurement period;
   (ii) representing the measured pulse signals as pulse signals oscillating around an average value thereof, and determining an envelope(signal)-curve for the pulse signals;
   (iii) determining a fit(envelope(signal))-function based on the envelope(signal)-curve, wherein the fit(envelope(signal))-function is determined based on a predetermined first functional prototype, and wherein the fit(envelope(signal))-function represents an idealised curve progression of the envelope(signal)-curve over the plurality of respiratory cycles without comprising pulse variations caused by ventilation or respiration induced heart-lung interaction;
   (iv) determining respiratory pulse variation signals corresponding to the pulse variations caused by ventilation or respiration induced heart-lung interaction over the plurality of respiratory cycles, wherein the determined respiratory pulse variation signals correspond to a difference between the envelope(signal)-curve and the fit(envelope(signal))-function;
   (v) determining an envelope(respiration)-curve for the respiratory pulse variation signals;
   (vi) determining a fit(envelope(respiration))-function based on the envelope(respiration)-curve, wherein the fit(envelope(respiration))-function is determined based on a predetermined second functional prototype, and wherein the fit(envelope(respiration))-function represents an idealised curve progression of the envelope (respiration)-curve over the plurality of respiratory cycles;

(vii) determining the indicator that is representative for the patient's volume responsiveness based on the fit (envelope(signal))-function and the fit(envelope(respiration))-function; and (viii) determining administration of the fluid based on the determined indicator.

2. Method according to claim 1, wherein the indicator that is representative for the patient's volume responsiveness is determined based on at least one parameter of the fit (envelope(signal))-function and at least one parameter of the fit(envelope(respiration))-function.

3. Method according to claim 1, wherein the indicator that is representative for the patient's volume responsiveness is determined based on a ratio between a maximum of the fit(envelope(signal))-function and a maximum of the fit (envelope(respiration))-function.

4. Method according to claim 1, wherein the sequence of measured pulse signals is detected over a time period of between ten seconds and three minutes.

5. Method according to claim 1, wherein the sequence of measured pulse signals is detected between two and ten subsequent respiratory cycles.

6. Method according to claim 1, wherein the envelope (signal)-curve is determined by continuously determining a distance dimension of the measured pulse signals from the average thereof and by then applying a low pass filter to a curve of determined distance dimensions, the low pass filter having a cutoff frequency below the pulse rate of the patient.

7. Method according to claim 1, wherein the predetermined first functional prototype is a non-negative smooth bell-shaped curve.

8. Method according to claim 1, wherein the predetermined first functional prototype comprises at least one parameter that is selected for curve fitting by any known optimization algorithm so as to achieve an optimal fitting of the fit(envelope(signal))-function to the envelope(signal)-curve.

9. Method according to claim 8, wherein a Levenberg-Marquardt algorithm is used to select the at least one parameter of the predetermined first functional prototype.

10. Method according to claim 1, wherein the respiratory pulse variation signals are determined in such a way that the respiratory pulse variation signals oscillate around an average value thereof.

11. Method according to claim 10, wherein a low pass filter is applied to the envelope(signal)-curve to determine the average value of the respiratory pulse variation signals, the low pass filter having a cutoff frequency below a respiratory frequency of the patient.

12. Method according to claim 1, wherein the envelope (respiration)-curve is determined by continuously determining a distance dimension of the respiratory pulse variation signals from an average value thereof and by then applying a low pass filter to a curve of determined distance dimensions, the low pass filter having a cutoff frequency below a respiration frequency of the patient.

13. Method according to claim 12, wherein the average value of the respiratory pulse variation signals is determined as moving average over a period of one respiration cycle of the patient.

14. Method according to claim 1, wherein the predetermined second functional prototype is a non-negative smooth bell-shaped curve, preferably a Cauchy-Lorentz function.

15. Method according to claim 1, wherein the predetermined second functional prototype comprises at least one parameter that is selected for curve fitting by any known optimization algorithm so as to achieve an optimal fitting of the fit(envelope(respiration))-function to the envelope(respiration)-curve.

16. Method according to claim 15, wherein a Levenberg-Marquardt algorithm is used to select the at least one parameter of the predetermined second functional prototype.

17. Method according to claim 5, wherein before applying the low pass filter the portion below the average value of the oscillating pulse signals is folded up to the portion above the average value of the oscillating pulse signals.

18. Method according to claim 5, wherein the distance dimension is defined as the squared signal or the difference between the extreme values of each pulse.

19. Method according to claim 1, wherein the envelope (signal)-curve is determined by connecting maxima and/or minima of the oscillating signal pulses.

20. Method according to claim 1, wherein the envelope (respiration)-curve is determined by connecting maxima and/or minima of the oscillating respiratory pulse variation signals.

* * * * *